(12) United States Patent
Kling

(10) Patent No.: US 6,193,828 B1
(45) Date of Patent: *Feb. 27, 2001

(54) METHOD OF PRODUCING STRIPS OF ELASTIC FILM FOR MANUFACTURING AN ABSORBENT PRODUCT

(75) Inventor: Robert Kling, Skene (SE)

(73) Assignee: SCA Hygiene Products Aktiebolag, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/849,883

(22) PCT Filed: Dec. 19, 1995

(86) PCT No.: PCT/SE95/01534

§ 371 Date: Jun. 17, 1997

§ 102(e) Date: Jun. 17, 1997

(87) PCT Pub. No.: WO96/19332

PCT Pub. Date: Jun. 27, 1996

(30) Foreign Application Priority Data

Dec. 21, 1994 (SE) .................................................. 9404436

(51) Int. Cl.$^7$ .................................................. A61F 13/49

(52) U.S. Cl. .................... 156/163; 156/73.3; 156/164; 156/229; 156/251; 156/259

(58) Field of Search ..................................... 156/163, 164, 156/229, 494–496, 73.3, 251, 259, 161

(56) References Cited

U.S. PATENT DOCUMENTS

| 444,821 | * | 1/1891 | Feister ............................... 156/554 X |
| 2,323,132 | * | 6/1943 | Hazell ................................... 156/259 |
| 2,391,539 | * | 12/1945 | Avery ................................... 156/259 |
| 3,356,556 | * | 12/1967 | Violette et al. .................. 156/259 X |
| 3,514,368 | * | 5/1970 | Netsel .............................. 156/259 X |
| 3,772,112 | * | 11/1973 | Lyons et al. .......................... 156/251 |
| 3,860,003 | | 1/1975 | Buell . |
| 4,300,562 | * | 11/1981 | Pieniak . |
| 4,407,284 | | 10/1983 | Pieniak . |
| 4,430,086 | * | 2/1984 | Repke ............................... 604/385.1 |
| 4,623,420 | * | 11/1986 | Hinkley ........................... 156/73.3 X |
| 4,626,305 | * | 12/1986 | Suzuki et al. ........................ 156/164 |
| 4,666,542 | * | 5/1987 | De Jonckheere ..................... 156/164 |

(List continued on next page.)

FOREIGN PATENT DOCUMENTS

| 1944326 | * | 4/1970 | (DE) .................................... 156/166 |
| 29 32 772 | | 2/1981 | (DE) . |
| 36 04 703A1 | | 9/1987 | (DE) . |
| 0 145 080A2 | | 6/1985 | (EP) . |
| 0 235 815A2 | | 9/1987 | (EP) . |
| 0 251 251A2 | | 1/1988 | (EP) . |
| 0 274 752A2 | | 7/1988 | (EP) . |
| 0 322 221A2 | | 6/1989 | (EP) . |
| 0 417 832A1 | | 3/1999 | (EP) . |
| 2 118 021A | | 10/1983 | (GB) . |
| 2 134 068A | | 8/1984 | (GB) . |
| 458 577 | | 4/1989 | (SE) . |

*Primary Examiner*—Jeff H. Aftergut
(74) *Attorney, Agent, or Firm*—Burns, Doane, Swecker & Mathis, L.L.P.

(57) ABSTRACT

The present invention relates to a method of producing a plurality of strips starting from a single sheet (1) of elastic film, wherein said single sheet (1) is fed in a longitudinal forward direction (X) up to a severing zone (b), in which the sheet is severed longitudinally into a plurality of strips (2–6), said plurality of strips then being fed further in the forward direction, while simultaneously being stretched in said longitudinal direction to thereby reduce their width (e) and thickness. The invention also relates to an absorbent product which makes use of a plurality of strips which are flat, thin and rectangular in one or more elasticated areas of said product to provide good and uniform breathing ability along said elasticated area(s).

19 Claims, 1 Drawing Sheet

U.S. PATENT DOCUMENTS

| | | |
|---|---|---|
| 4,687,477 | 8/1987 | Suzuki et al. . |
| 4,693,771 * | 9/1987 | Payet et al. .................... 156/73.3 X |
| 4,762,582 * | 8/1988 | de Jonckheere .................... 156/164 |
| 4,816,094 | 3/1989 | Pomplun et al. . |
| 4,938,754 | 7/1990 | Mesek . |
| 5,104,714 | 4/1992 | Leiber et al. . |
| 5,429,694 * | 7/1995 | Herrmann ............................ 156/164 |
| 5,500,075 * | 3/1996 | Herrmann ........................ 156/164 X |
| 5,728,011 * | 3/1998 | Sugimoto et al. ............... 156/170 X |

* cited by examiner

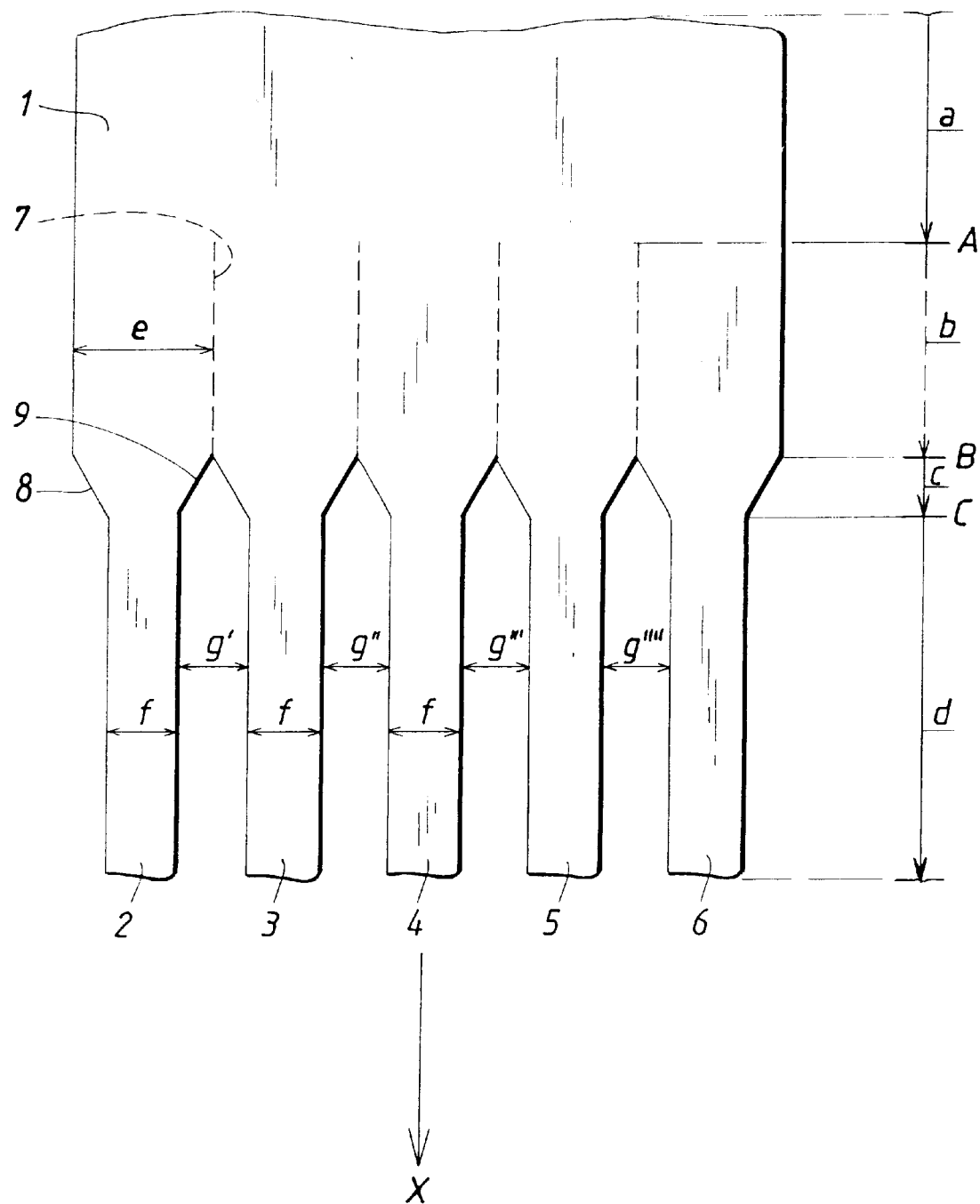

METHOD OF PRODUCING STRIPS OF ELASTIC FILM FOR MANUFACTURING AN ABSORBENT PRODUCT

FIELD OF THE INVENTION

The present invention relates to a method of producing a plurality of strips of elastic film starting from a single sheet of elastic film and to an absorbent article for absorbing human exudate, in which said strips are attached in an area to be elasticated.

PRIOR ART

In some prior art absorbent articles e.g. U.S. Pat. No. 3,860,003, a strip of rubber material is applied in a zone of the article which is to be elasticated so that it affords a better fitting for the user and thus provides increased comfort as well as helping to prevent leakage. Such elasticated zones however give rise to many problems such as pressure on the wearer's leg due to the strip which is kept as narrow as possible to save material, yet still wide enough to give a sufficient tension to provide a good fit in all positions of movement. A further problem arises in that the strip itself is made of rubber and thus does not provide a "breathable" material (i.e. a material constructed so as to allow moisture from the body's skin to escape). Since the strip is relatively wide, this can often result in certain areas of the body often being wet which may result in soreness, loss of the skin's resistance to abrasion and even infection.

To solve this problem of moisture release, it is however known in the art to use films of elastic material which are able to "breathe". Such films are however more expensive and offer only a limited breathing ability in the best of cases. Although relatively thin strips are available (e.g. down to about 6 mm width), handling problems result when trying to use such small strips which makes them impractical for this purpose. Moreover when supplied, each single roll of thin strip must be separately packed which results in wastage as well as greater expense.

As a solution to pressure zones on the wearer's thighs and to improve moisture release, the document U.S. Pat. No. 4,687,477 proposes a solution which replaces the single wide strips in the elasticated leg areas of an absorbent garment by a series of between three and forty-five rubber strands laid side-by-side along the areas to be elasticated. Whilst said rubber strips allow good breathing ability due to the spaces between them, rubber however has the disadvantage of being quite a heavy material. Additionally, rubber is a moulded product and thus a certain thickness has to be maintained in order to obtain a level of uniformity in the rubber strand which provides adequate resistance against breakage. Such thickness in turn increases weight even further. Far more importantly however, since the strips of rubber must be divided later into separate strands and moved laterally apart with respect to each other for application to the product, the mouldings are formed as individual moulded strands of rubber which are held together in a manner which is intrinsically separable. This intrinsic separability is brought about by a weak rubber fusion between adjacent strands, for example by spraying talcum powder onto the individual strands and then allowing a light contact between them. This requirement for separability is however very problematic since the weakness of the inter-strand bond is difficult to control accurately. If the strength is too low (i.e. a very weak bond) this may result in premature splitting of the joint between the strands and, if it is too strong, one of the strands may be torn during attempted separation from the adjacent strand. In either case, the resultant loose strands become difficult to deal with and, when this happens during operation in the machine, the resultant stoppage is very costly, especially in the field of absorbent article manufacture where the production speed is very high (e.g. a belt speed of about 200 m/min).

The present invention thus seeks to provide a means of elastication which gives good breathing ability in the area of elastication, is thin and light and which can be handled without the risk of premature separation of the strands. Thus, when the strips are applied to an absorbent article, the article can be made lighter and cheaper than hitherto.

SUMMARY OF THE INVENTION

The aforementioned problems are solved by the features of the invention.

Preferred features of the invention are defined in the dependent claims.

By adopting the method of the invention, the individual strips produced remain combined as a single sheet of uniform-thickness film having no joints formed on the material before severing into individual strips. This allows easier handling and the avoidance of any measures concerning joint strength control between the individual strips. The film sheet and resultant strips can thus be very thin (e.g. between 5 and $120\mu$) since there are no separable joints. Moreover, merely by stretching the film after passing through a severing zone, each of the resultant strips becomes narrower and simultaneously forms an intermediate free zone between the strips without any lateral movement. This zone will allow moisture to escape in an elasticated zone of an article, on which the strips are subsequently applied.

The finished absorbent article fitted with such strips will thus have "breathable" elasticated portions which can thus be made very lightweight in comparison to prior art articles.

BRIEF DESCRIPTION OF THE DRAWING

A preferred embodiment of the invention will now be described in more detail with reference to the accompanying FIGURE, in which an enlarged, schematic plan view of a sheet of elastic film is depicted during processing from being an undivided elastic film through to being a plurality of separated and stretched strips for subsequent attachment to an absorbent article.

DETAILED DESCRIPTION OF A PREFERRED EMBODIMENT

A single sheet 1 or web of air-impermeable elastic film is continuously passed from its supply roll (not shown) through zones "a" to "d" which will be described in more detail later.

The film may be of any suitable material as long as it is sufficiently elastically deformable without risk of tearing. However the film is preferably very thin e.g. with a thickness of between 10 and $150\mu$ in the relaxed state. Examples of suitable films may be those made of elastomers based on polystyrene/elastomer block copolymers such as S-B-S, S-EB-S and S-I-S. Other suitable films may be made of e.g. EVA, EBA or EPDM. Preferably the film will also have an elastic extensibility of over 100% (i.e. it can be extended elastically by 100% or more with respect to its relaxed dimension).

Zone "a" ends at line "A" which is in line with the upper part of the plurality of dotted lines 7. A second zone "b", ending at line B, is a zone in which the elastic sheet is separated into a plurality of strips of width "e" by severing the single sheet longitudinally at one or more locations across the width of said sheet. Said locations are denoted by the dotted lines 7 in the figure.

Severing of the sheet may occur in several ways. For instance, a plurality of rotating circular discs may be positioned on one side of the sheet, each of said discs having a cutting edge arranged in the plane of the sheet 1 and bearing against an underlying support surface. Such cutting discs may be e.g. 1 mm wide and thus may be conveniently used side by side. As an alternative an ultrasonic cutter may be used, as known per se. Other suitable cutting methods will be obvious to a person skilled in the art.

Whilst four separate severing locations have been depicted by each of the four lines 7, and thus producing five strips 2, 3, 4, 5 and 6, the number of locations may vary according to requirements. Each of the widths "e" will preferably be the same and thus, in the shown example, each strip will have a width "e" of about 6 mm when starting from a sheet of about 30 mm width.

The feeding of the sheet may occur in any suitable manner, driven roller pairs nipping the sheet therebetween being one appropriate example. Such feeding means should however be appropriately arranged so that the sheet 1 is fed in its forward longitudinal direction (see arrow X) in a taught, yet substantially unstretched condition throughout the zones "a" and "b", by applying only a low tension to the sheet. In this way, the film sheet 1 will thus have a substantially uniform thickness and width throughout these zones.

Zone "c" starts at line "B". Suitable means, such as a roller operated at a lower speed than the other driven roller pairs, is provided in line with line "B" and serves to provide a resistive force to the movement of the strips 2–6 downstream of line "B". The severed strips are fed in the direction X at their leading edge by suitable means such as a roller pair or by the attachment of the strips to the products on a moving production line for example.

Due to the feeding which is counteracted by said resistive force, each of the strips are stretched in the longitudinal direction so that their width will change from width "e" to width "f" over the length of zone "c". Each of the strips whilst in zone "c" will thus have its two edges 8 and 9 converging until width "f" is reached. Width "f" is the final width of each of the individual strips 2 to 6 to be applied to the absorbent product.

As can be seen in the figure, the contraction of the width of the strips in zone "c" causes the strips to be come spaced between adjacent edges so that a spacing of width g is formed between the two strips 2 and 3 for example.

Similarly a gap of g", g''' and g'''' is formed between the strips 3, 4, 5 and 6 as shown. The spacing between the strips is preferably constant throughout zone "d" such that each strip is rectangular. In a preferred embodiment, the width of the strips 2 to 6 is also constant.

The final width of the sheet of film 1 after stretching and including the spacing between each strip is given by the formula:

$$\text{Final width} = M(1-((1-k)/N))$$

where k=contraction coefficient
M=original width of non-stretched film
N=number of strips after splitting It should also be noted that not only the width but also the thickness of each strip will decrease during stretching. Thus it will be appreciated that the resultant strips may be very thin (e.g. down to $5\mu$) and very narrow (e.g. down to as low as 1 or 2 mm) but secure production of the individual strips is possible due to the fact that the strips started as a single sheet. For present day requirements, a strip width of 3mm in stretched condition is suitable, although the strip width can be varied within large limits.

With the individual strips 2 to 6 in an extended condition (zone "d") and spaced by a distance "g", the plurality of strips is applied to a product in a zone designated to be elasticated, and attached appropriately. Moreover due to the inter-strip spacing, a breathing space has been provided between each strip without any lateral movement having been effected.

The invention also concerns absorbent articles such as nappies or sanitary pads which per se are well known. Such articles generally comprise an impermeable backing layer as well as a permeable top sheet designed for contact with the body, between which an absorbent is placed (e.g. a core of cellulose pulp with super absorbent polymer). In order to provide a good fit during movement, elasticated zones are provided e.g. in the portions designed to be around the wearer+s thighs or waist. In order to provide an elasticated zone, the strips in zone "d" (see above) are thus attached to the article in a gathered or non-gathered condition (in a manner known per se) and, due to their inherent elasticity, provide an elastic zone. Due to the inter-strip spacing "g", no lateral movement of the strips is required to obtain a product which thus has a breathable elasticated zone which is furthermore made of a particularly light elastic film.

Since the strips may be constant in width along their length if the stretching is constant, they will thus have a spacing which is constant between adjacent strips which provides a uniform breathing ability along the whole length of the elasticated zone.

Where a certain number of strips is provided on opposite sides of the absorbent product, two sheets 1 will normally be used for either side to avoid any lateral movement forces on the thin strips. However, the strips may for example be divided into two sections in a non-stretched (or low-stretched) zone and then directed to either side of the product before being severed and stretched. In the least preferred embodiment, the sheet may be severed and stretched into strips which are lead in respective groups to either side of the product whilst maintaining the inter-strip spacing of each group.

The final thickness of the strips may be as low as $5\mu$ up to about $100\mu$, although a thickness of between $10\mu$ and $40\mu$ is suitable. Similarly, a suitable width would be between 2 and 16 mm in the stretched condition and preferably between 3 and 8 mm.

The elasticated zone may also be the belt or waist zone of an absorbent article.

In a further embodiment, strips may be provided which present a fibrous material surface on one side (which has advantages per se). To accomplish this, the non-porous elastic sheet may also be attached to a fibrous covering material to provide a combined sheet before the severing zone and thus the fibrous material will be held substantially intact by each of the continuous strips even in the stretched condition.

A further advantageous embodiment of the invention is its application in providing a split band giving good breathing ability in connection with absorbent products made in a "longitudinal" direction. As is known in the art, absorbent garments may be produced lying top end (waist end) to bottom end in the direction of conveyor belt travel which is called longitudinal production, or they may lie transverse to the longitudinal direction which is called transverse production.

When producing absorbent products in longitudinal production, the making of e.g. seams and the application of e.g. leg elastic in the longitudinal direction is a relatively simple matter since synchronisation is uncomplicated. However, when applying a material layer or forming a seam in the transverse direction is required particular difficulties result.

One particular example concerns the application of waist elastic in the form of a foam sheet or the like. In order to achieve elastication and application of the strip in this condition, the strip has to be cut into the form of a patch or the like and then stretched before being applied and attached to the waist area. EP-A-0 338 662 shows an example of an apparatus which is designed to perform such an operation. The apparatus comprises two circular discs angled to the vertical, each of said discs having pins thereon for receiving one end of a pre-cut strip in the position of closest separation of the discs and, by rotation of the discs to a position of furthest separation, the strip is stretched and can then be applied in this stretched condition to an absorbent product.

To provide an elasticated waistband in this area which consists of a plurality of thin strips (in the manner defined above with respect to the method of the invention) in order to provide a waist area which has a good breathing ability, is very difficult since stretching and applying of many individual strips leads to many difficulties. Consequently, when using longitudinal production, the waist bands are often produced by using a broad strip of material instead. With the method of the invention however, a solution to this problem is provided in that the separate waist band elastic patches can be provided with ends which are non-severed, so as to allow application to e.g. the pins of the discs (see e.g. pins 15 in EP 0 338 662), yet the middle part of the elastic portion between the ends (e.g. starting from 1 or 2 cm from each end) will be severed in one or more locations (i.e. corresponding to the lines 7 in the figure). In this way, the patch can be applied, as previously, to the disc pins or the like without difficulty and, upon stretching the individual strip portions of the patch will contract in width and thickness so as to provide an appearance as in zone "d" of the figure.

Thus a stretched patch will be produced on the discs having two non-severed ends (such as in zone "a") joined by a plurality of strips (such as in zone "d"). This strip will then be applied in the stretched condition to the waist region and attached thereto.

Since the patches are discrete entities which are to be applied to the waist portion of said article, said patches may be produced using a method as shown in only zones "a" and "b" of the figure, but where the severing means are only operated intermittently so as to sever only the required areas, leaving sequential leading and trailing non-severed ends. Such a method then allows the web of attached patches to be rolled up on to a further reel for later use if such is required. When applying the patches in longitudinal production, the reel is unwound and, by appropriate means, is cut into separate patches which are then rotated through 90° and individually attached to the pins on the rotating discs (as in EP-A-0 338 662) for stretching and application. To avoid the requirement of a 90° rotation, the patches may alternatively be severed between their ends (still leaving two non-severed ends) by use of multiple cutters which are synchronised with the movement of the film.

Whilst the invention has been described above with respect to a preferred embodiment thereof, the invention is not limited thereto and it will be appreciated that many variations of the invention are possible within the scope of the appended claims. For example, other materials and applications are possible.

What is claimed is:

1. A method of producing a flexible absorbent article having an elasticated area, the method comprising the steps of:

providing a continuous single sheet of a film of uniform thickness, and the single sheet does not have any separable joints therein;

feeding said sheet in a longitudinal forward direction to a severing zone, severing said sheet longitudinally into a plurality of strips, feeding said plurality of strips further in the forward direction simultaneously while stretching in said longitudinal direction to thereby reduce their width and thickness to achieve spacing between each of the strips by virtue of their reduced width, and applying, while each of the plurality of strips is still in its stretched and spaced condition, said plurality of strips to a sheet of an absorbent article in an area which is to be elasticated, said strips being fixedly attached to said absorbent article either simultaneously with their application or shortly thereafter.

2. A method of producing a flexible absorbent article having an elasticated area, the method comprising the steps of:

providing a continuous single sheet of a film of uniform thickness and which does not have any separable joints therein;

feeding said sheet in a longitudinal forward direction to a severing zone, severing said sheet longitudinally into a plurality of strips, feeding said plurality of strips further in the forward direction simultaneously while stretching in said longitudinal direction to thereby reduce their width and thickness to kachieve spacing between each of the strips by virtuec of their reduced width so that the plurality of strips do not contact each other, and applying, while each of the plurality of strips is still in its stretched and spaced condition, said plurality of strips to a sheet of an absorbent article in an area which is to be elasticated, said strips being fixedly attached to said absorbent article either simultaneously with their application or shortly thereafter, wherein said applying step occurs after the severing and feeding steps, and all of the strips are applied to the sheet of the absorbent article while the strips are still attached to the single sheet.

3. Method according to claim 2, wherein the width of said strips is reduced to a constant width after passing through an initial stretching zone.

4. Method according to claim 2, wherein each of said strips has substantially the same constant width after the initial stretching zone.

5. Method according to claim 4, wherein at least three strips are produced having a spacing between opposing edges of adjacent strips, and wherein said spacing is constant along the length of the strips.

6. Method according to claim 2, wherein each strip has a substantially constant width along its entire length and is separated from an adjacent strip by a distance which is substantially constant along the length of each strip.

7. Method according to claim 2, wherein said strips have a thickness of between 5 and 100$\mu$ when applied to the product.

8. Method according to claim 2, wherein said strips have a width of between 2 and 16 mm when applied to the product.

9. Method according to claim 2, wherein said absorbent article is an absorbent garment, and said strips are applied to the waist portion of said absorbent garment.

10. Method according to claim 2, wherein said absorbent article is an absorbent garment, and said strips are applied to portions of said absorbent garment designated to surround the legs or thighs of the wearer.

11. Method according to claim 2, wherein said strips have a thickness of between 20 and 40μ when applied to the product.

12. Method according to claim 2, wherein said strips have a width of between 3 and 8 mm when applied to the product.

13. Method according to claim 2, wherein the single sheet is severed with a cutting tool.

14. Method according to claim 13, wherein the cutting tool is a rotary disc.

15. Method according to claim 13, wherein said cutting tool is an ultrasonic cutter.

16. Method according to claim 2, wherein said single sheet is of a substantially uniform thickness.

17. Method according to claim 16, wherein said single sheet is of a uniform thickness.

18. Method according to claim 2, wherein the single sheet does not have any separable joints that extend in the longitudinal direction of the single sheet that may enable separating the single sheet into longitudinal strips.

19. Method according to claim 2, wherein the single sheet has a thickness in the range of 5 and 120μ.

* * * * *